US00PP13749P29

(12) United States Plant Patent
Lemon

(10) Patent No.: US PP13,749 P2
(45) Date of Patent: Apr. 29, 2003

(54) GERANIUM PLANT NAMED 'GLOBAL DEEP LILAC'

(75) Inventor: David Lemon, Santa Barbara County, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 10/245,471

(22) Filed: Sep. 17, 2002

(51) Int. Cl.[7] ..... A01H 5/00

(52) U.S. Cl. ..... Plt./332

(58) Field of Search ..... Plt./332

*Primary Examiner*—Kent Bell
(74) *Attorney, Agent, or Firm*—Webb Ziesenhiem Logsdon Orkin & Hanson, P.C.

(57) ABSTRACT

A new and distinct free flowering ivy geranium plant with distinctive bright lilac colored flowers with striking dark orchid eye above medium green foliage. The new variety exhibits superior heat tolerance over other ivy geranium varieties known to the inventor.

1 Drawing Sheet

BOTANICAL CLASSIFICATION

*Pelargonium×peltatum* (ivy geranium).

VARIETAL DENOMINATION

'Global Deep Lilac'.

BACKGROUND OF THE INVENTION

The present invention comprises a new and distinct cultivar of *Pelargonium×peltatum* known by the varietal name 'Global Deep Lilac'. The new variety was discovered in a selected breeding program in Lompoc, Calif. as Breeder No. 5DG1683-2. The new variety is a result of cross breeding of 'Butterfly' (female, unpatented) and 'Cindy' (male, unpatented). The new variety exhibits a similar flower type to 'Cindy' and a similar flower color to 'Butterfly' yet with much better heat tolerance than either parent. The new variety was first asexually reproduced by cuttings in Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of 12 weeks from a rooted cutting to flowering in a 10 inch pot. The response time was determined on plants grown in soilless media employing constant fertilizer 200–250 parts per million of nitrogen and potassium in full light. Three cuttings planted in a pot and pinched at four weeks produce a finished hanging basket.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out by Oglevee, Ltd. in Connellsville, Pa. Plants described were about 8 weeks from a rooted cutting. The color readings were taken on a plant under 65–75 foot candles of fluorescent cool white light. Color references are primarily to The R.H.S. Colour Chart of The Royal Horticultural Society of London.

PLANT

Form: Compact, cascading mound.
Height: 13–17 cm from media surface to top of foliage in a 4 inch pot.
Diameter: 20 cm.
Strength: Does not require artificial support.
Rooting time: Roots visible to outside of a dirt plug in 10–14 days.
Leaves:
- *Attachment.*—Alternate.
- *Stipules.*—Two per node.
- *Size.*—Length: 7–9 cm. Width: 5–6 cm. Zone: 1 cm from petiole attachment; zone is 5 mm wide.
- *Shape.*—Reniform; cordate base.
- *Apex.*—Somewhat rounded.
- *Margin.*—Entire lobed.
- *Texture.*—Rubbery, highly reflective, shiny.
- *Pubescence.*—Very fine.
- *Color.*—Upper surface: 137A. Lower surface: 144A. Zone: 177A, more noticeable on younger leaves.
- *Ribs and veins.*—Venation: Palmate. Color: 144A.

Petioles:
- *Color.*—144A.
- *Length.*—3.5–5 cm.

Stem:
- *Color.*—144A.
- *Internode length.*—1–5 cm.

THE BUD

Shape when no color showing:
- *Overall.*—Elongated, elliptical cluster.
- *Individual bud.*—Elliptical or oval.

Size when no color showing:
- *Overall.*—2–3.5 cm across cluster.
- *Individual bud.*—1–1.2 cm long; 5–6 mm wide.

Number of buds per cluster: 6–11.
Color: 75C with markings of 59C.
Pubescence: Long hairs.

INFLORESCENCE

Blooming habit: Continuous flowering throughout growing season; free and early flowering.
Size of umbel: 8–10 cm in diameter.
Borne: Umbel, flowers on pedicel, pedicel on peduncle, 7–10 cm above foliage.
Flowers:
*Form.*—Flat to slightly cupped; ruffled, semi-double.
*Number of flowers per umbel.*—5–9.
*Size.*—Diameter: 4.7–5.2 cm wide; 2.5 cm long. Depth: 1–1.5 cm.
Petals:
*Color.*—Upper surface: 75A with some petals shading to 75C at the middle.
Lower surface: 75B overall. Some petals exhibit 75A at outer edge shading to 75C toward the center and 75D at the base of the petal. Veining shows through. Eye: Not present on all petals and varies in size and color when present. Each flower has at least 2 petals with a large eye on them. The eye color ranges between 59A, 61A, 74A, 71A, and 73A. Shape: Oval to heart shaped. Size: 2.3–3.0 cm long; 1.7–2.2 cm wide. Apex: Rounded. Base: Pointed. Margin: Entire. Number per flower: 9–12. Texture and appearance: Highly reflective, smooth, velvety.
*Tonality from a distance.*—Bright lavender blossoms with striking dark orchid eye above medium green foliage.
Petaloids:
*Quantity.*—0–7.
*Shape.*—Irregular; twisted; tubular; petal shaped; long narrow; some holding pollen.
*Color.*—Same as petals.
Pedicel:
*Length.*—3.5–3.9 cm.
*Color.*—144A and 187B.
Peduncle:
*Length.*—8–13 cm.
*Color.*—144A.
Lasting quality: Umbels last 7–14 days.
Disease/pest resistance: No unusual susceptibility to diseases or pests has been noted to date.

REPRODUCTIVE ORGANS

Stamens:
*Anthers.*—2–3 mm.
*Filaments.*—Length: 0.6–1.2 cm. Color: White with lavender. Pollen: Orange.
Pistils:
*Number.*—One.
*Length.*—1.2 cm.
*Stigma.*—Color: Orchid/dark lavender.
*Style.*—0.5–0.7 cm long.
*Ovaries.*—Superior, pubescent, 0.6–0.7 cm long, 2 mm wide, green.
Fruit: None observed.

I claim:

1. A new and distinct variety of geranium plant substantially as shown and described.

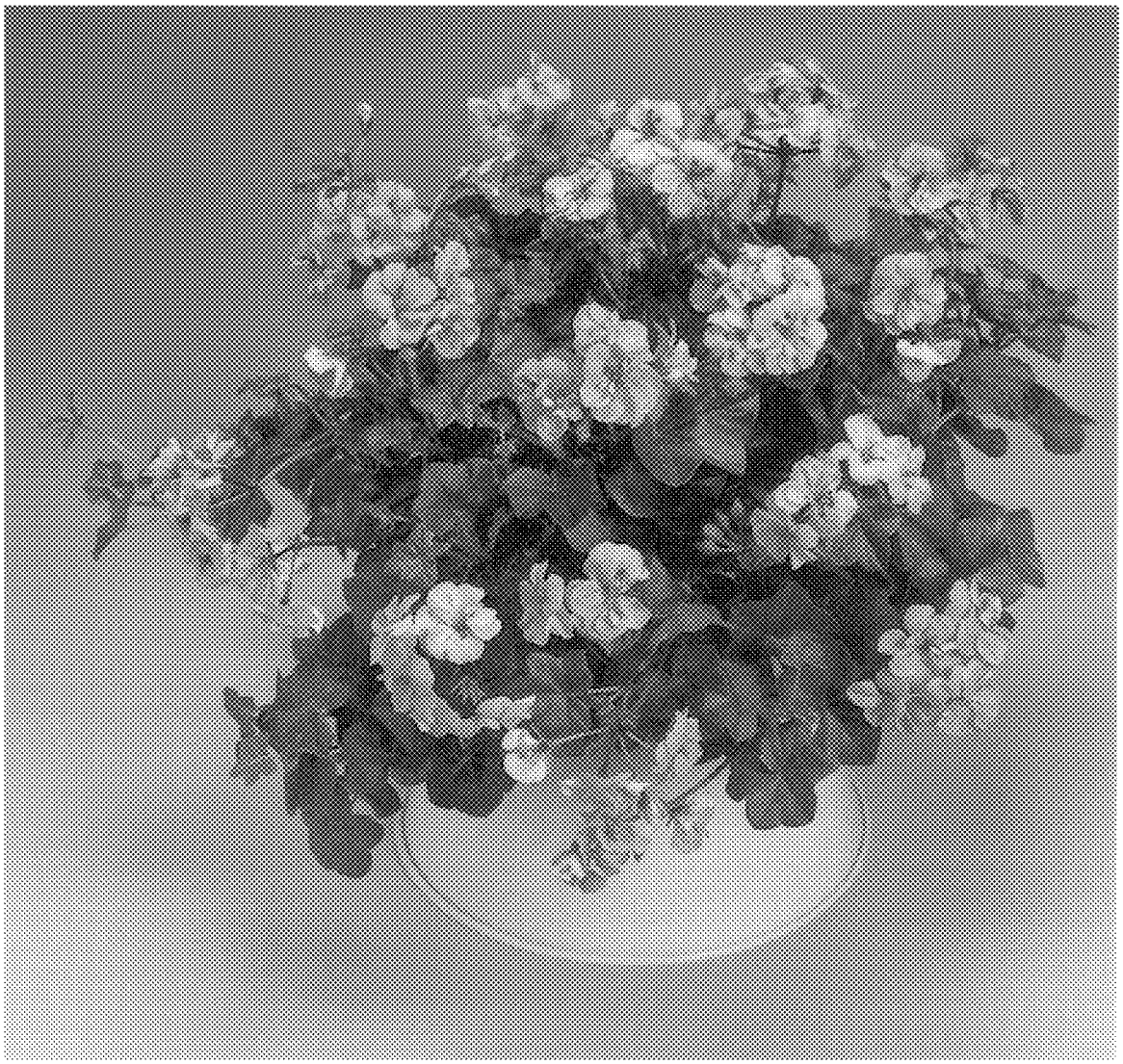

* * * * *